United States Patent [19]
Chaisson et al.

[11] Patent Number: 5,449,362
[45] Date of Patent: Sep. 12, 1995

[54] GUIDING CATHETER EXCHANGE DEVICE

[76] Inventors: Gary A. Chaisson, 300 Liberty St.;
Craig M. Walker, 312 Keystone Loop, both of Houma, La. 70360

[21] Appl. No.: 89,892

[22] Filed: Jul. 9, 1993

Related U.S. Application Data

[63] Continuation of Ser. No. 810,489, Dec. 19, 1991, abandoned.

[51] Int. Cl.⁶ .............................................. A61B 17/00
[52] U.S. Cl. ...................................... 606/108; 604/93; 604/264; 604/280
[58] Field of Search ................... 606/108; 604/93, 264, 604/280

[56] References Cited

U.S. PATENT DOCUMENTS

| | | | |
|---|---|---|---|
| 4,616,648 | 10/1986 | Simpson | 606/108 |
| 4,744,366 | 5/1988 | Jang | 606/194 |
| 4,748,982 | 6/1988 | Korzewski et al. | 604/160 X |
| 4,762,129 | 8/1988 | Bonzel | 604/96 |
| 4,824,435 | 4/1989 | Giesy et al. | |
| 4,846,193 | 7/1989 | Tremulis et al. | |
| 4,875,489 | 10/1989 | Messner et al. | |
| 4,932,413 | 6/1990 | Shockey et al. | |
| 4,944,745 | 7/1990 | Sogard et al. | 604/96 |
| 4,947,864 | 8/1990 | Shockey et al. | |
| 4,966,163 | 10/1990 | Kraus et al. | |
| 4,976,689 | 12/1990 | Buchbinder et al. | |
| 4,988,356 | 1/1991 | Crittenden et al. | |
| 5,031,636 | 7/1991 | Gambale et al. | |
| 5,035,686 | 7/1991 | Crittenden et al. | 604/243 X |
| 5,052,386 | 10/1991 | Fischer, Jr. | 128/207.15 |
| 5,061,273 | 10/1991 | Yock | 604/96 |
| 5,131,407 | 7/1992 | Ischinger et al. | 604/282 |
| 5,234,407 | 8/1993 | Teirstein et al. | |

Primary Examiner—Stephen C. Pellegrino
Assistant Examiner—Jeffrey A. Schmidt
Attorney, Agent, or Firm—Pravel, Hewitt, Kimball & Krieger

[57] ABSTRACT

A guiding catheter exchange device allows the exchange of a coronary guiding catheter while the coronary guide wire is left in place across an obstruction in the coronary artery. In performing percutaneous transluminal coronary angioplasty, a guiding catheter is placed selectively into either the right or left coronary artery. The guide wire is advanced down the coronary artery and across the obstruction. The exchange device of the present invention allows the guiding catheter to be exchanged and while the wire is still in position across the obstruction. The exchange device has a short bore at its distal end portion which allows the exchange device to be routed into the patient's artery upon the coronary guide wire. The exchange device then provides adequate structure and support for exchanging different size guiding catheters.

22 Claims, 5 Drawing Sheets

GUIDING CATHETER EXCHANGE DEVICE

This application is a continuation of application Ser. No. 07/810,489, filed Dec. 19, 1991, now abandoned.

BACKGROUND OF THE INVENTION

1. Field of the Invention

The present invention relates to cardiac catheter devices and more particularly relates to an improved method and apparatus for cardiac catheter devices utilized in the performance of percutaneous transluminal coronary angioplasty procedures and the like. Even more particularly, the present invention relates to an improved catheter device which allows the exchange of a coronary guiding catheter while the coronary guide wire is left in place and across an obstruction in the coronary artery.

2. General Background

In the mid 1970s, Andreas Gruntzig first used a balloon catheter to percutaneously dilate a stenosis within the coronary artery of a patient with coronary artery disease. Since that time, the utilization of percutaneous transluminal coronary angioplasty has increased significantly. Recently, newer procedures such as coronary stent implantation and coronary atherectomy are being used more and more frequently as an adjunct to coronary angioplasty.

These procedures oftentimes require the use of a larger guiding catheter having a hollow bore. Typically, a guiding catheter with an internal diameter ranging from about 0.060 inches to about 0.080 inches or greater can be utilized. On occasion, the guiding catheter must be exchanged for one of a different distal shape or which is larger in both internal and/or external diameter.

At present such procedures require a removal of the balloon catheter and the coronary guide wire before a new guiding catheter can be placed. After the guiding catheter has been exchanged, the coronary artery and the blockage must be recrossed with the coronary wire. This results in significant risk. Oftentimes, the coronary stenosis has been pre-dilated resulting in intimal flaps and cracks in the wall of the vessel. When recrossing the obstruction, the wire sometimes follows a course underneath the dissection and forms a sub-intimal tract in the wall of the blood vessel.

It is therefore desirable to not recross the obstruction with a coronary guide wire when exchanging the coronary guiding catheter.

SUMMARY OF THE PRESENT INVENTION

The apparatus of the present invention provides a guiding catheter exchange device that will allow the exchange of the guiding catheter without having to remove the coronary guide wire. The apparatus of the present invention is of an overall length of about two hundred to three hundred centimeters (200–300) (for example) providing a short (e.g. three to ten (3–10) centimeters) distal tip, and a larger diameter mid section of about 0.060 inches in diameter. The apparatus provides a lumen or bore that extends a partial distance from the distal tip such as for example about sixty to seventy centimeters (60–70 cm) to a position just proximal to the 0.060 inch larger diameter segment.

The proximal segment can be reinforced such as with a reinforcing core of wire, such as for example a metal wire core that extends past the bore or lumen. This core wire can be tapered at its distal end portion. The proximal segment could be in the form of an extruded, one piece polymer.

The short distal tip is placed in the coronary artery and is flexible. Therefore, it causes little or no trauma to the coronary artery. The larger diameter mid portion is reinforced so that the guiding catheter will tract appropriately around the aortic arch without pulling the guide catheter exchange device from the coronary ostium. Alternately, the larger diameter mid portion can be of a shape similar to the aorta and/or similar to the shape of the guiding catheter. This helps prevent the system from pulling the coronary guide wire out of the coronary artery during exchange.

The proximal portion of the guiding catheter exchange device is smaller in diameter such as for example about 0.03 inches in diameter than that portion that exits the femoral artery during use. Its smaller diameter allows the insertion of the currently available arterial sheath utilized for percutaneous transluminal coronary angioplasty.

Reinforcement of the distal end portion of the guiding catheter exchange device can be accomplished by wrapping a metallic wire around the distal end portion. For example, any suitable polymeric plastic catheter can be used for the guiding catheter exchange device. A 0.030 inch plastic catheter would thus be reinforced for a short distance along the distal end portion by wrapping, for example a 0.015 inch metal wire around the shaft.

The bore of the guiding catheter exchange device could be for example a 0.018 inch internal diameter. The wire is attached to the catheter with an adhesive that is appropriate. The polymeric plastic utilized would preferably be non-compliant in that it would preferably not stretch along its axis and at the same time be flexible.

In performing percutaneous transluminal coronary angioplasty, a guiding catheter is placed selectively into either the right or left coronary artery. A guide wire (for example 0.018 or 0.014 inch diameter) is then gently advanced down the coronary artery and across the obstruction. A balloon catheter is then advanced over this guide wire and centered on the obstruction. The balloon is inflated and then deflated, then pulled back into the guiding catheter.

If the guiding catheter does not provide enough support to cross the obstruction, a new guiding catheter with a different distal tip is sometimes required. Often times, after the balloon has successfully crossed the obstruction and been inflated, there are dissections that occur in the region of the obstruction. This may require the implantation of a coronary stent or coronary atherectomy device.

Both of these procedures require the introduction of a different guiding catheter. The guiding catheter exchange device of the present invention would be advanced across the coronary guide wire via the guiding catheter in place. After it has been properly positioned into the coronary artery, the guiding catheter is withdrawn from the patient over the guiding catheter exchange device. After the guiding catheter has been totally removed from the patient, the guiding catheter exchange device is held in place in the coronary artery.

If a guiding catheter that is larger in diameter is required, the sheath in the femoral artery is then removed and a larger sheath is placed over the guiding catheter exchange device in the femoral artery. The technician or cardiologist is then ready to advance the new guiding catheter over the guiding catheter exchange device.

After the new guiding catheter is selectively or coaxially placed onto the coronary ostium, the guiding catheter exchange device is then removed while leaving the coronary guide wire in place and crossing the obstruction. At this point, the cardiologist can then proceed to balloon angioplasty, stent implantation or atherectomy, or other like procedure.

The present invention thus provides a guiding catheter exchange device for use in the performance of percutaneous transluminal angioplasty procedures. The apparatus includes a coronary guiding catheter with a lumen and with an end portion that can be placed in a patient's aorta. A coronary guiding angioplasty wire is provided and a guiding catheter exchange device is insertable into the lumen of the guiding catheter and also provides a bore so that the guiding catheter exchange device fits over the guide wire enabling the guiding catheter to be positioned without removal of the guide wire.

In the preferred embodiment, the guiding catheter has an internal bore of between about 0.060 and 0.080 inches or greater.

In the preferred embodiment, the guiding catheter exchange device has an enlarged diameter portion positioned near the distal tip portion of the guiding catheter exchange device.

The guiding catheter exchange device preferably provides an elongated proximal portion with an internal stiffener. The stiffener can be an internal wire member and is preferably an internal metallic wire member that extends longitudinally along the proximal end portion of the guiding catheter exchange device. The stiffener needs to possess stiffness stiffener to prevent kinking at the level of the femoral artery.

In the method of the present invention, a method of exchanging a coronary guiding catheter during an angioplasty procedure comprises the steps of first inserting a guide wire into the patient's vascular system. The wire is then removed and the guiding catheter is placed coaxially in the coronary ostium. A coronary guide wire is then advanced across the coronary obstruction. The balloon catheter is then advanced over the coronary guide wire. If the balloon catheter does not produce the desired result, it is then removed from the patient over the coronary guide wire. A guiding catheter is advanced, tracking over the guide wire. When an exchange of the guiding catheter is desired, the guiding catheter exchange device is inserted into the patient's vascular system over the coronary guide wire but inside the first guiding catheter. The first guiding catheter is then removed, leaving the guide wire and exchange device in position. A second guiding catheter is then inserted over the guiding catheter exchange device and tracking upon the coronary guide wire until the second guiding catheter approaches a position adjacent the obstruction. In the method, the exchange can be accomplished wherein the wire maintains a position that crosses the obstruction at all times.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
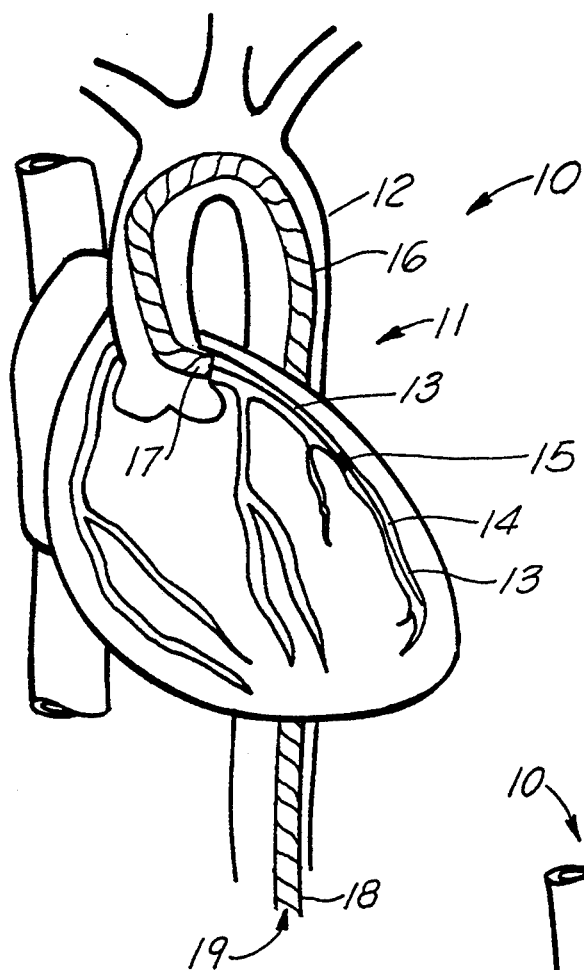
FIG. 1 is a schematic view illustrating the method of the present invention by placement of the guide wire and guiding catheter.

In FIG. 1, there can be seen a patient's heart 11, the aorta 12 and the coronary artery 14. An elongated coronary guide wire 13 has been inserted in FIG. 1 into the aorta 12 and also extending into the coronary artery 14 crossing an obstruction 15. The guide wire 13 is thus the first portion of the apparatus 10 of the present invention inserted into the patient's vascular system.

Figure 2:
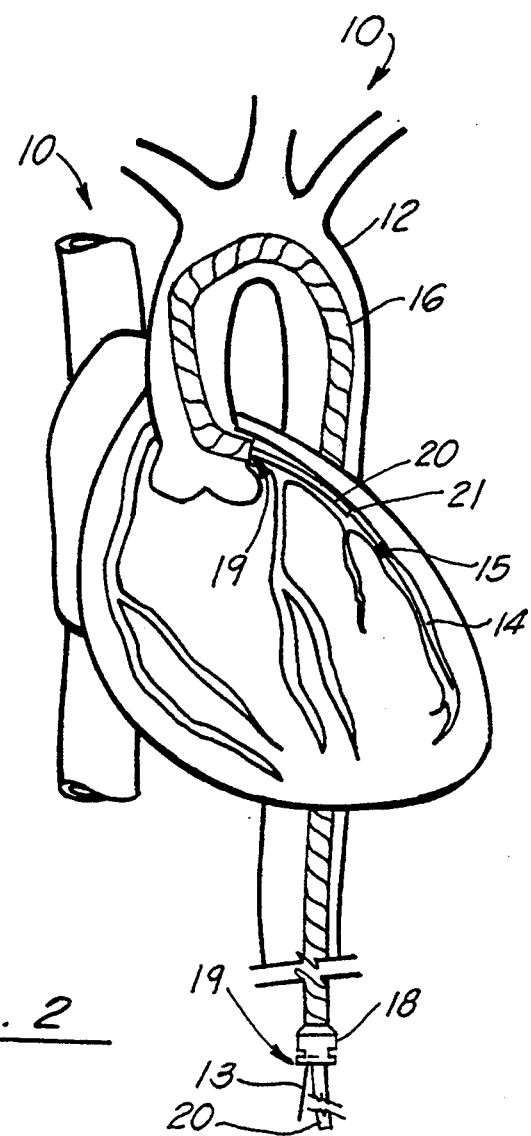
FIG. 2 is a schematic view of the preferred method of the present invention illustrating positioning of the guide wire, guiding catheter, and guiding catheter exchange device.

After the wire 13 is placed in the position shown in FIG. 1, a first guiding catheter 16 is advanced to a position adjacent the obstruction 15 as shown in FIGS. 1 and 2. For the reasons mentioned above in the General Discussion portion of the specification, it is sometimes necessary to exchange the guiding catheter 16. The first guiding catheter 16 shown in FIGS. 1 and 2 will thus be exchanged for a second guiding catheter 34 which is shown in FIG. 5.

Figure 3:
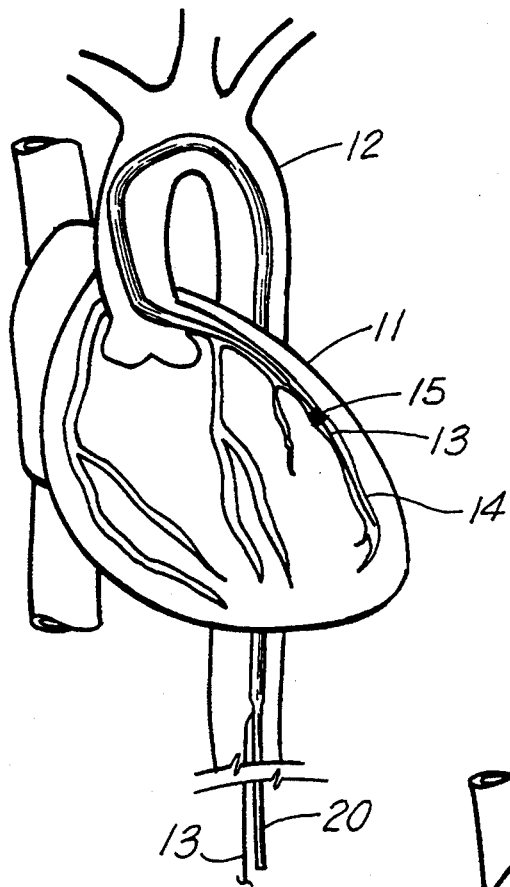
FIG. 3 illustrates the method of the present invention after removal of the first guiding catheter.
Figure 4:
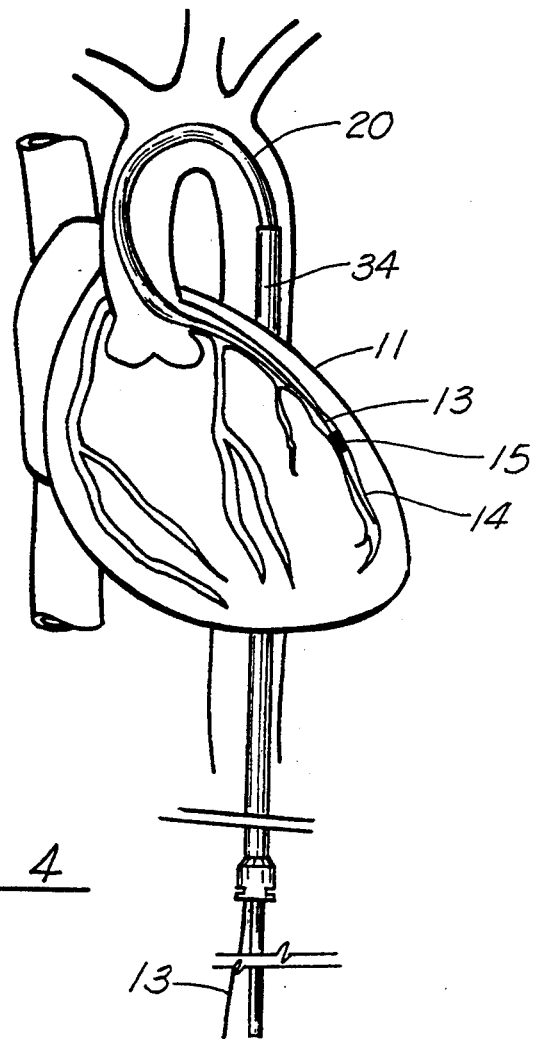
FIG. 4 is a schematic view illustrating the method of the present invention during installation of the second guiding catheter.

The first guiding catheter 16 has a distal end portion 17 and a proximate end portion 18 which is maintained in a position externally of the patient, exiting the patient's femoral artery for example. Thus, the portion 18 rests outside the patient's body so that the cardiologist can access the obstruction 15 using a balloon catheter inserted at the proximate end 18 of the guiding catheter 16. The guiding catheter 16 has a hollow bore 19 which receives the wire 13 as well as any balloon catheter or the like inserted into the bore 19. In FIG. 2, exchange catheter 20 has been inserted into the bore 19 of guiding catheter 16. As part of the method of the present invention, the exchange catheter 20 is advanced over the coronary wire 13 and inside of the bore 19 of guiding catheter 16 until the distal end 21 of exchange catheter 20 is positioned adjacent obstruction 15. The exchange catheter 20 (FIGS. 5-9 and 10-13) preferably carry a radiopaque marker 22 at the distal end 21 portion. This allows fluoroscopic examination to determine the position of the distal end 21 at all times. In FIG. 3, the first guiding catheter 16 has been removed and therefore only the guide wire 13 and the exchange catheter 20 are in position. In FIG. 4, a second guiding catheter 34 is shown advancing upon the exchange catheter 20. Thus, the exchange catheter 20 is routed into the patient's coronary artery 14 upon the guide wire 13 and the exchange catheter 20 provides adequate support for placement of the second guiding catheter of a different size for example into position.

Figure 5:
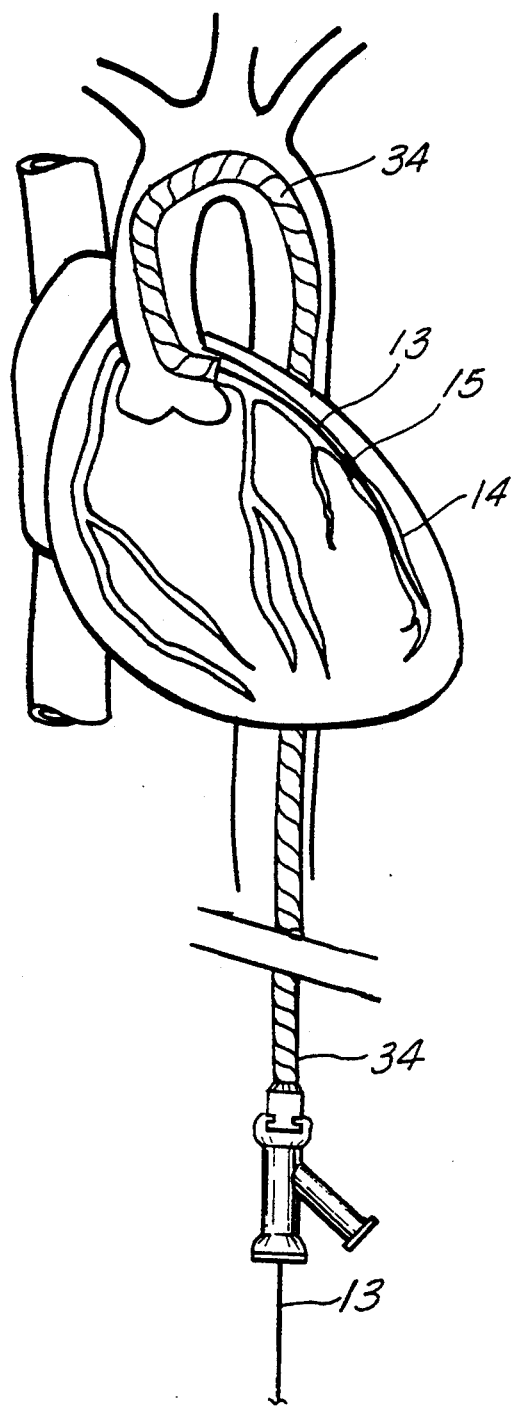
FIG. 5 is a schematic view illustrating removal of the guiding catheter exchange device after a second guiding catheter has been positioned.
Figure 9:
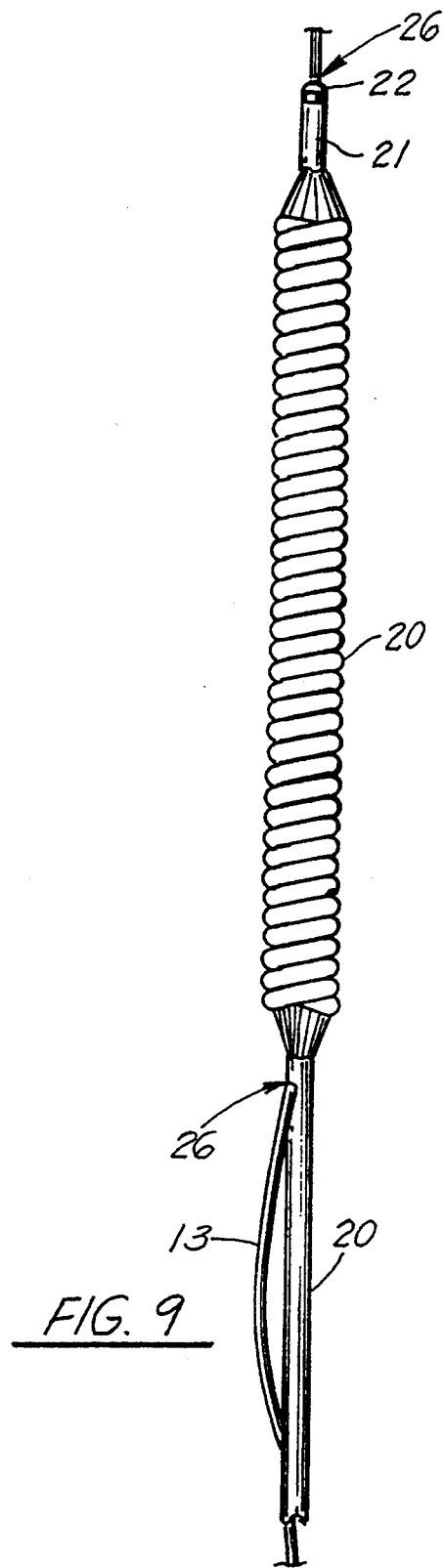
FIG. 9 is a side view of the preferred embodiment of the apparatus of the present invention.
Figure 6:
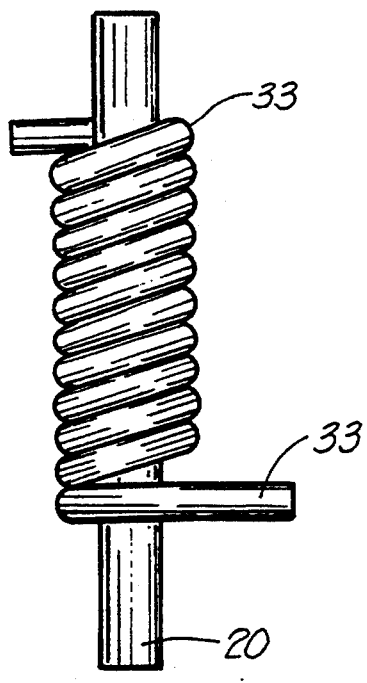
FIG. 6 is a fragmentary view of the preferred embodiment of the apparatus of the present invention.

In FIG. 5, second guiding catheter 34 is in operative position and the exchange catheter has been removed. During this entire procedure, the guide wire 13 has been maintained in its position crossing the obstruction 15 in the coronary artery 14.

FIGS. 6–9 illustrate a preferred construction of the guiding catheter 20. The exchange catheter 20 has an enlarged diameter section 23 that begins at cylindrical section 24 and gradually enlarges in diameter at annular tapered shoulder 25 and gradually reduces diameter at annular tapered shoulder 29. An opening 27 is provided at recess 28 for exit of bore or lumen 26 that extends continuously between opening 28 and distal end 22 of exchange catheter 20. Thus, during use the guiding catheter 20 is inserted into the patient's vascular system by threading the proximate end of guide wire 13 into bore 26. Thus, the enlarged end portion 23 of guiding catheter 20 tracks into the patient's vascular system upon guide wire 13 and while guide wire 13 is maintained in its operative position and across obstruction 15. By exiting guide wire 13 and bore 26 at recess 28, this allows minimum friction between the guide wire 13 and the bore 26. Further, this allows the placement of a stiffener 31 in the form of an elongated longitudinally extending wire 31 which gives sufficient strength to the catheter 20 so that it will support a new second guiding catheter 34 during insertion. Additionally, it allows the exchange procedures to take place with a device of manageable length reducing the possibility of contamination.

Figure 8:
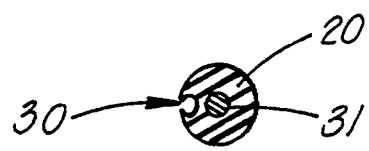
FIG. 8 is a section view taken along lines 8—8 of FIG. 7.
Figure 7:
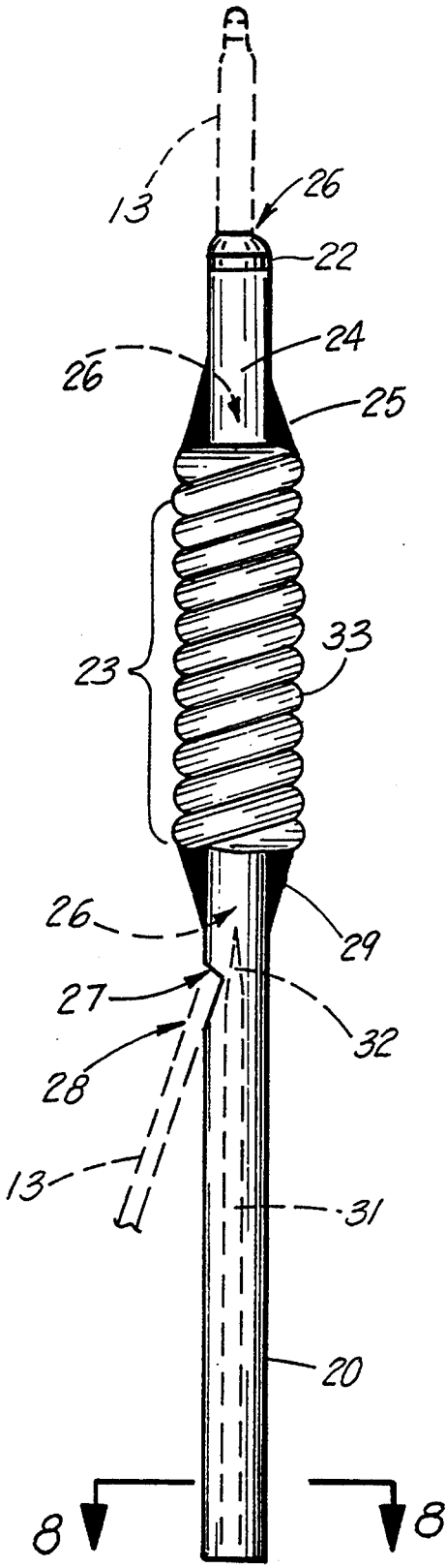
FIG. 7 is a side schematic partial view of the preferred embodiment of the apparatus of the present invention.
Figure 10:
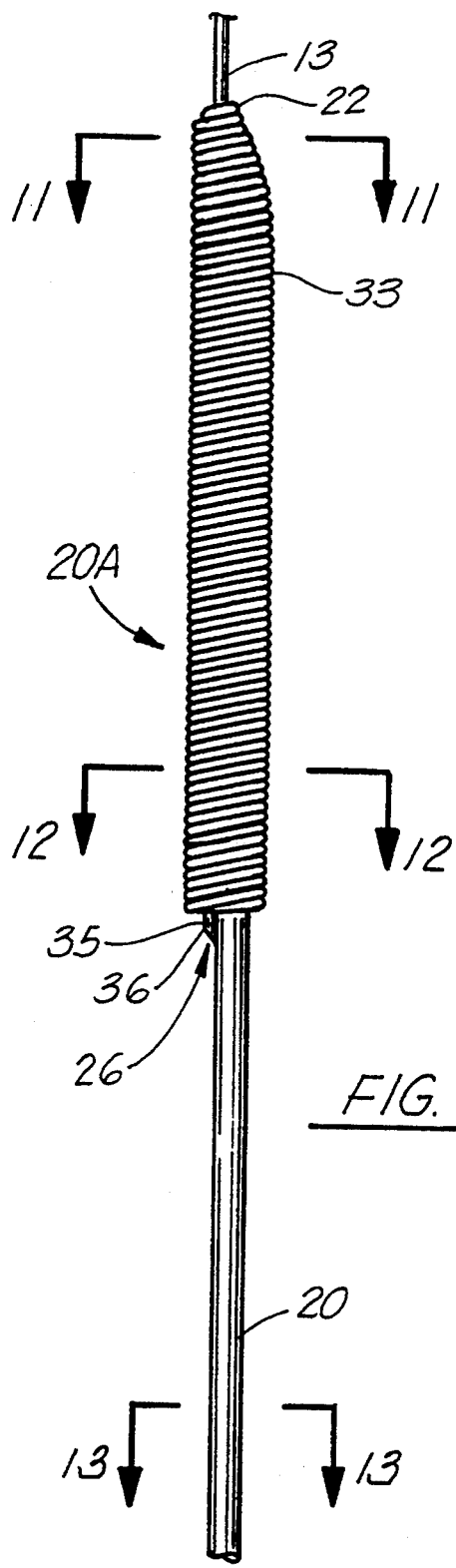
FIG. 10 is another partial side view of the preferred embodiment of the apparatus of the present invention.
Figure 11:
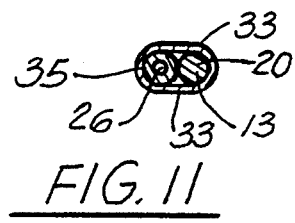
FIG. 11 is a sectional view taken along lines 11—11 of FIG. 10.
Figure 12:
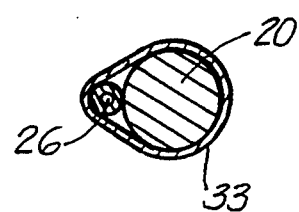
FIG. 12 is a sectional view taken along lines 12—12 of FIG. 10.
Figure 13:
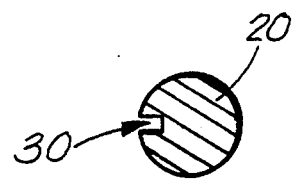
FIG. 13 is a sectional view taken along lines 13—13 of FIG. 10.

An elongated longitudinally extending slot 30 can be provided on the external surface of catheter 20 as shown in FIG. 8 for supporting the majority of the length of wire 13 by simply placing the wire 13 in the slot 30.

The enlarged section 23 can be reinforced with a coiled reinforcement wire 33. Alternatively, the enlarged end portion 23 can be in the form of a single extruded polymer, i.e. a one piece structure having two longitudinally extending bores, one to accommodate wire 13 and another to carry the stiffener wire 31.

FIGS. 10–13 show an alternate construction of the exchange catheter, which is designated generally by the numeral 20A. In the embodiment of FIGS. 10–13, the bore 26 is in a tubular member 35 which is spaced from the catheter 20, both the tubular member 35 and catheter 20 being wrapped with coil wire 33 as shown. This allows the tubular member 35 to carry the bore 26 beginning at distal end 22 and exiting at the proximate end 36 of tubular member 35.

The following table lists the part numbers and part descriptions as used herein and in the drawings attached hereto.

| Part Number | PARTS LIST Description |
|---|---|
| 20 | guiding catheter exchange device |
| 11 | patient's heart |
| 12 | aorta |
| 13 | coronary guide wire |
| 14 | coronary artery |
| 15 | obstruction |
| 16 | first guiding catheter |
| 17 | distal end guiding catheter |
| 18 | proximate end guiding catheter |
| 19 | bore of catheter |
| 21 | distal end exchange catheter |
| 22 | radiopaque marker |
| 23 | enlarged diameter end portion |
| 24 | cylindrical section |
| 25 | annular tapered shoulder |
| 26 | lumen of exchange catheter |
| 27 | opening |
| 28 | recess |
| 29 | annular tapered shoulder |
| 30 | longitudinally extending slot |
| 31 | internal wire stiffener |
| 32 | tapered end wire stiffener |
| 33 | coil reinforcement |
| 34 | second guiding catheter |
| 35 | tubular member |
| 36 | proximal end |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method for performing a coronary procedure on a patient comprising the steps of:
   (a) selectively positioning a guide catheter into a coronary artery of the patient;
   (b) positioning a coronary guide wire through a lumen of the guide catheter, out the distal end of said guide catheter and into the coronary artery;
   (c) positioning a guide catheter exchange device over the guide wire while the guide wire is positioned in the lumen of the guide catheter so that a distal end of said guide catheter exchange device extends distally of the distal end of the guide catheter while a proximal portion of said guide catheter exchange device extends proximally outside the patient's body;
   (d) withdrawing said guide catheter proximally over said guide catheter exchange device and entirely out of the patient's body while maintaining the distal end of the guide catheter exchange device in position in the coronary artery;
   (e) after withdrawing the guide catheter, positioning a second guide catheter over the proximal portion of the guide catheter exchange device; and
   (f) advancing the second guide catheter over the guide catheter exchange device and into the coronary artery, wherein
   said guide catheter exchange device has a length relative to the guide catheter such that during steps (c) and (d) the proximal portion of the guide catheter exchange device outside the patient's body is greater than the length of the guide catheter, and the proximal portion of the guide catheter exchange device is smaller in diameter than the distal portion.

2. A method for performing a coronary procedure on a patient comprising the steps of:
   (a) selectively positioning a guide catheter into a coronary artery of the patient;
   (b) positioning a coronary guide wire through a lumen of the guide catheter, out the distal end of said guide catheter and into the coronary artery;
   (c) positioning a guide catheter exchange device over the guide wire while the guide wire is positioned in the lumen of the guide catheter so that a distal end of said guide catheter exchange device extends distally of the distal end of the guide catheter while a proximal portion of said guide catheter exchange device extends proximally outside the patient's body;
   (d) withdrawing said guide catheter proximally over said guide catheter exchange device and entirely out of the patient's body while maintaining the distal end of the guide catheter exchange device in position in the coronary artery;
   (e) after withdrawing the guide catheter, removing a first sheath in a femoral artery, placing a larger sheath over the guide catheter exchange device into the femoral artery, and positioning a second, larger guide catheter over the proximal portion of the guide catheter exchange device; and
   (f) advancing the second, larger guide catheter over the guide catheter exchange device and into the coronary artery,
   said guide catheter exchange device having a length relative to the guide catheter such that during steps (c) and (d) the proximal portion of the guide catheter exchange device outside the patient's body is greater than the length of the guide catheter.

3. In combination,
   a coronary guide catheter;
   a coronary guide wire removably and slidably positioned in a lumen of the coronary guide catheter and extending out a distal end thereof; and
   a guide catheter exchange device comprising:
   (a) a distal portion comprised of a tubular member defining a guide wire lumen therethrough and having proximal and distal guide lumen openings communicating with the guide wire lumen of the guide catheter exchange device;
   (b) a proximal portion comprised of an elongate member, said proximal portion connected to the distal portion, said proximal and distal portions having a combined length greater than that of the coronary guide catheter, said proximal portion being smaller in diameter than the distal portion,
   said guide catheter exchange device being removably and slidably positioned in the lumen of the coronary guide catheter with the guide wire removably and slidably positioned in the guide wire lumen of the guide catheter exchange device whereby the guide catheter can be exchanged for another guide catheter while the guide wire is maintained in position in a coronary artery of a patient.

4. The invention of claim 3 in which the proximal portion of the guide catheter exchange device further comprises:
   a stiffening core.

5. The invention of claim 4 in which the stiffening core of the guide catheter exchange device further comprises:
   a reinforced core of wire.

6. The invention of claim 3 in which the distal portion of the guide catheter exchange device comprises:
   a coiled reinforced wire.

7. The invention of claim 3 in which the distal portion of the guide catheter exchange device comprises:
   an extruded polymer tube.

8. The invention of claim 3 in which the guide catheter exchange device further comprises:
   an internal stiffener to provide resistance to kinking.

9. The invention of claim 8 in which the internal stiffener of the guide catheter exchange device extends through the proximal portion and at least partially into the distal portion.

10. The invention of claim 8 in which the internal stiffener of the guide catheter exchange device extends through the proximal portion and the distal portion.

11. The invention of claim 8 in which the internal stiffener of the guide catheter exchange device is tapered.

12. The invention of claim 8 in which the internal stiffener of the guide catheter exchange device is tapered distally.

13. The invention of claim 3 in which the guide catheter exchange device has a length of approximately 200–300 centimeters.

14. The invention of claim 3 in which the length of the guide wire lumen is approximately 60–70 centimeters.

15. The invention of claim 3 in which the distal portion is approximately 0.06 inches in diameter.

16. The invention of claim 3 in which the guide catheter exchange device further comprises:
    a distal tip located distally of the distal portion.

17. The invention of claim 16 in which the distal tip of the guide catheter exchange device is approximately 3–10 centimeters in length.

18. An intravascular accessory for use in conjunction with a coronary procedure on a patient, said accessory adapted to facilitate the exchange of a first coronary guide catheter for a second coronary guide catheter, the accessory comprising:
    a distal portion comprised of a tubular member defining a guide wire lumen therethrough and having proximal and distal guide lumen openings communicating with the guide wire lumen, the guide wire lumen having a length of 60–70 cm; and
    a proximal portion comprised of an elongate member, said proximal portion connected to the distal portion, said proximal and distal portions having a combined length sufficiently greater than that of either the first or second coronary guide catheter to allow the complete withdrawal and exchange of the first guide catheter for the second guide catheter while maintaining the distal portion of the guide catheter exchange device in the patient, wherein the proximal portion is smaller in diameter than the distal portion that is positioned into the coronary artery during use.

19. An intravascular accessory for use in conjunction with a coronary procedure on a patient, said accessory adapted to facilitate the exchange of a first coronary guide catheter for a second coronary guide catheter, the accessory comprising:
    a distal portion comprised of a tubular member defining a guide wire lumen therethrough and having proximal and distal guide lumen openings communicating with the guide wire lumen, the guide wire lumen having a length of 60–70 cm; and a proximal portion comprised of an elongate member, said proximal portion connected to the distal portion, said proximal and distal portions having a combined length sufficiently greater than that of either the first or second coronary guide catheter to allow the complete withdrawal and exchange of the first guide catheter for the second guide catheter while maintaining the distal portion of the guide catheter exchange device in the patient, wherein the proximal portion has a diameter of approximately 0.03 inches.

20. In combination,
a coronary guide catheter;
a coronary guide wire removably and slidably positioned in a lumen of the coronary guide catheter and extending out a distal end thereof; and
guide catheter exchange device comprising:
 (a) a distal portion comprised of a tubular member defining a guide wire lumen therethrough and having proximal and distal guide lumen openings communicating with the guide wire lumen of the guide catheter exchange device;
 (b) a proximal portion comprised of an elongate member, said proximal portion connected to the distal portion, said proximal and distal portions having a combined length greater than that of the coronary guide catheter, wherein
said guide catheter exchange device is removably and slidably positioned in the lumen of the coronary guide catheter with the guide wire removably and slidably positioned in the guide wire lumen of the guide catheter exchange device whereby the guide catheter can be exchanged for another guide catheter while the guide wire is maintained in position in a coronary artery of a patient, and
the distal portion of the guide catheter exchange device comprises:
 a single extruded polymer having two longitudinally extending bores.

21. In combination,
a coronary guide catheter;
a coronary guide wire removably and slidably positioned in a lumen of the coronary guide catheter and extending out a distal end thereof; and
a guide catheter exchange device comprising:
 (a) a distal portion comprised of a tubular member defining a guide wire lumen therethrough and having proximal and distal guide lumen openings communicating with the guide wire lumen of the guide catheter exchange device;
 (b) a proximal portion comprised of an elongate member, said proximal portion connected to the distal portion, said proximal and distal portions having a combined length greater than that of the coronary guide catheter;
 (c) a longitudinally extending slot on an external surface of the guide catheter exchange device, wherein
  said guide catheter exchange device is removably and slidably positioned in the lumen of the coronary guide catheter with the guide wire removably and slidably positioned in the guide wire lumen of the guide catheter exchange device whereby the guide catheter can be exchanged for another guide catheter while the guide wire is maintained in position in a coronary artery of a patient.

22. The invention of claim 21, wherein:
at least a portion of the guide wire is located in said slot.

* * * * *